United States Patent
Albrecht

(12) 
(10) Patent No.: US 6,472,373 B1
(45) Date of Patent: *Oct. 29, 2002

(54) COMBINATION THERAPY FOR ERADICATING DETECTABLE HCV-RNA IN ANTIVIRAL TREATMENT NAIVE PATIENTS HAVING CHRONIC HEPATITIS C INFECTION

(75) Inventor: Janice K. Albrecht, Winter Park, FL (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/311,487

(22) Filed: May 13, 1999

Related U.S. Application Data

(63) Continuation-in-part of application No. 09/079,566, filed on May 15, 1998, now abandoned, and a continuation-in-part of application No. 08/935,123, filed on Sep. 22, 1997, now abandoned, and a continuation-in-part of application No. 08/938,033, filed on Sep. 21, 1997, now Pat. No. 6,172,046.

(60) Provisional application No. 60/085,669, filed on May 15, 1998.

(51) Int. Cl.$^7$ .......................... A61K 31/70; H01N 43/04

(52) U.S. Cl. ........................... 514/43; 514/42; 514/894; 424/85.4; 424/85.7

(58) Field of Search .................. 424/85.4, 85.5, 424/85.6, 85.7; 514/43, 885, 893, 894, 42; 435/5; 536/23.52

(56) References Cited

U.S. PATENT DOCUMENTS

| | | | |
|---|---|---|---|
| RE29,835 E | 11/1978 | Witlowski et al. | ............. 536/29 |
| 4,211,771 A | 7/1980 | Witlowski et al. | ........... 424/180 |
| 4,530,901 A | 7/1985 | Weissmann | ................... 435/70 |
| 5,503,828 A | 4/1996 | Testa | |
| 5,767,097 A | 6/1998 | Tam | ............................. 514/43 |
| 5,849,800 A * | 12/1998 | Smith | ......................... 514/647 |
| 6,063,772 A | 5/2000 | Tam | ............................. 514/43 |
| 6,172,046 B1 * | 1/2001 | Albrecht | ...................... 514/43 |

FOREIGN PATENT DOCUMENTS

| | | | |
|---|---|---|---|
| EP | 0 707 855 A2 * | 4/1996 | |
| EP | 0 707855 A2 | 4/1996 | |
| WO | WO 95/13090 | * | 5/1995 |
| WO | WO 96/36351 | * | 11/1996 |

OTHER PUBLICATIONS

Reichard et al. 1997 Hepatology 26: Suppl 1 pp. 108S–111S.*

Reichard et al. Jan./Feb., 1998 The Lancet vol. 351 pp. 83–87.*

AIDS Weekly, Aug. 21, 1995 (PROMT database Acc No: 95:285149).*

McHutchison et al. Nov. 1998, New England Journal of Medicine 339 (21) pp. 1485–1492.*

Schalm et al. 1997 Journal of Hepatology 26 pp. 961–966.*

Gish 1999 Canadian Journal of Gastroenterology 13(1) pp. 57–62.*

Main 1995 Journal of Hepatology 23 (Suppl 2) 32–36.*

Chemello et al. J of Hepatology 1994; 21 (Suppl 1). Abstract No. GS 5/29, p. S12.*

Oshita et al. Igaku–no–Ayumi. May 3, 1997; 181 (5): 337–340. (provided in IDS).*

Bizollon et al. Hepatology. 1994; 21, Suppl. 1: S58, abstract only. (provided in IDS).*

Lai, et al. Symposium to the 9$^{th}$ Biennial Scientific Mtg., Asian Pacific Assoc. for the Study of the Liver—1994.

Brouwer, et al., Journal of Hepatology 21 (Suppl 1) 1994, S17, Abstract No. WP2/08.

The Merck Index, 11$^{th}$ ed., Compound No. 8199.

Dusheiko, et al., Hepatology, vol. 20, No. 4, Pt. 2, 1994, Abstract No. 440.

Bodenheimer et al., Hepatology, vol. 20, No. 4, Pt. 2, 1994, Abstract No. 441.

Bisceglie, et al., Hepatology, vol. 16, No. 3, 1992, 649–654.

Kakyumu, et al., Gastroenterology 1993: 105–507–512.

Marcellin, et al., Bailliere's Clinical Gastroenterology, vol. 8, No. 2, Jun. 1994, 233–253.

Brillanti, et al., J. Hepatol 18 (Suppl 1) 1993, S101, Abstract No. T–69.

Sambataro, J. Hepatol. 18 (Suppl. 1) 1993, S167, Abstract No. T–377.

Wu, et al., Antiviral Re.(Suppl 1) 1993, S167, Abstract No. 228.

Cavalletto, L., et al., Congress Proceedings from Ital. J. Gastroeterol., 25, 443–68 Abstract at p. 452 (Venezia, Nov. 11–13, 1993).

Brillanti, et al., Gastroenterology 1994: 107:812–817.

Brillanti, Hepatology 18 (4 Part 2) 1993; 150A, Abstract No. 375.

Lai, et al., Hepatology 18 (4 Part 2) 1993; 150A, Abstract No. 146.

Chemello, et al., Journal of Hepatology 21 (Suppl 1) 1994, S12, Abstract No. GS 5/29.

Package Insert for Intron A–Interferon alfa–2b Recombinant, 1992, Schering Corporation, Kenilworth, NJ.

(List continued on next page.)

Primary Examiner—Mary K. Zeman
Assistant Examiner—Shanon A. Foley
(74) Attorney, Agent, or Firm—Thomas D. Hoffman

(57) ABSTRACT

Methods for treating an antiviral treatment naive patient having chronic hepatitis C infection to eradicate detectable HCV-RNA involving administering a therapeutically effective amount of a combination therapy of ribavirin and interferon-alpha for a time period of from 20 up to 50 weeks are disclosed.

19 Claims, No Drawings

OTHER PUBLICATIONS

Schvarcz, et al., J. Med Virology, vol 46 (1995) pp. 43–47.

Braconier, et al., Scand J. Infectious Dis vol 27 (1995) pp. 325–39.

Bizollon, T., et al., Revue Francaise De Castro–Enterologie Apr. 1994. No. 297 vol. XXX 429 English & French Language Versions.

Schvarcz, et al., Journal of Hepatology vol. 23 (1995) (Suppl 2) pp. 17–21.

Chemello, et al., ibid 23 (1995) (Suppl 2) pp. 8–12.

Lai, et al., *Gastroenterology*, Nov. 1996, vol. III, pp. 1307–1312.

Sats, et al., NS5A Region and the Prediction of Interferon Effect, Igaku–no–Ayumi (May 3, 1997), vol. 181, (No. 5) pp. 330–340 (Translation).

Hayashi, N., *Today's Therapy*, Chronic Hepatitis, Konnichi–no–Chiryo–Sisin, Jan. 15, 1997, p. 403 (Translation).

Gunther, R., "What is Ribavirin?" and "Combination with Ribavirin for Non–Responders", Medical Tribune, Nr 22, May 30, 1997, www.hepatitis–c.de/wasriba.htm (in German).

Schalm, SW., et al., Digestive Diseases and Sciences, vol. 41, (No. 12) Dec. 1996, Supplement, pp. 131S to 134S.

Reichard, O.., et al., "Interferon–Alpha and Ribavirin versus Interferon alpha as Therapy for Chronic Hepatitis C—A randomized Double–blind placebo–controlled study." American Association for the Study of Liver Diseases, 1996 Annual Meeting, www.hepatitis–c.de/riba.htm.

Pol, S., et al., "Ribavirin–Interferon v. Interferon alone in Non–Responders to IFN in Chronic Hepatitis C", American Association for the Study of Liver Diseases, 1996 Annual Meeting,. www.hepatitis–c.de/riba.htm.

Lurie, Y., et al., "Ribavirin Interferon Combination for chronic HCV", American Gastroenterology Association Digestive Disease Week meeting in Washington, May 1997, www.hepatitis–c.de/riba.htm.

Bellobuono, A., et al. "Ribavirin and interferon–alph combination therapy v. interferon–alpha alone in the treatment of chronic hepatitis C; A randomized clinical trial;" Journal of Viral Hepat 1997; vol. 4, 185–191.

Weiland, et al., "Combination Treatment with Interferon Alpha–2b and Ribavirin in Patients Suffering from Chronic Hepatitis C Relapsing After, or Not Responding to Earlier Treatment with Interferon," Translation of Abstract from Lakarstamman (Swedish Physicians' Meeting) Stockholm—Dec. 1993.

El Zayadi, et al., "Combination treatment of alpha interferon–2b and ribavirin in chronic hepatitis C genotype"< Hepatology 22 (4 Pt 2), 152A (1995).

Bizollon, et al., "Ribavirin and Interferon treatment for Hepatitis C recurrence [sic] Following Orthotopic Liver Transplantation", Abstract, *Hepatology* 21 Suppl 1, p. S58 (1994).

Martinot–Peignoux, M., et al., Hepatology (1995) vol. 22, pp. 1050–1056.

Brillanti, S., et al, J. Hepatology (1995) vol. 23 (Suppl. 2) pp. 13–16.

Lurie, Y., et al, Gastroenterology (1997) vol. 112 (4), p. A1325.

Lurie, Y., et al. J. Hepatology (1997) vol. 26 (Suppl. 1) Abstract C01/223, p. 233.

* cited by examiner

COMBINATION THERAPY FOR ERADICATING DETECTABLE HCV-RNA IN ANTIVIRAL TREATMENT NAIVE PATIENTS HAVING CHRONIC HEPATITIS C INFECTION

This application is a continuation-in-part of commonly-owned U.S. patent application Ser. No. 09/079,566, filed May 15, 1998, now abandoned; which claims priority to commonly-owned U.S. Provisional Patent Application Serial No. 60/085,669, filed May 15, 1998, now abandoned; and a continuation-in-part of commonly-owned U.S. patent application Ser. No. 08/938,033, filed Sep. 21, 1997, now U.S. Pat. No. 6,172,046 and a continuation-in-part of commonly-owned U.S. patent application Ser. No. 08/935,123, filed Sep. 22, 1997 now abandoned.

BACKGROUND OF THE INVENTION

The present invention relates to methods for treating an antiviral treatment naive patient having chronic hepatitis C infection to eradicate detectable HCV-RNA involving a combination therapy using a therapeutically effective amount of a combination therapy of ribavirin and interferon-alpha for a time period of from 20 up to 50 weeks.

Chronic infection with hepatitis C virus is an insidious and slow-progressing disease having a significant impact on the quality of life. It can eventually result in cirrhosis of the liver, decompensated liver disease and/or hepatocelluar carcinoma.

Alpha interferon monotherapy is commonly used to treat chronic hepatitis C infection. However, this treatment is not always effective and sometimes results in intolerable side effects related to the dosage and duration of therapy. Ribavirin has been proposed as a monotherapy treatment for chronic hepatitis C infection (Thomas et al. AASLD Abstracts, Hepatology Vol. 20, NO. 4, Pt 2, Number 440, 1994). However, this monotherapy treatment has usually been found ineffective. Combination therapy of alpha interferon and ribavirin has been proposed: (Lai, et al. Symposium to the 9th Biennial Scientific Meeting Asian Pacific Association for the Study of the Liver. 1994); Combination treatment with interferon alpha-2b and ribavirin for chronic hepatitis C in patients who have failed to achieve sustained response to interferon alone: Swedish experience. *J Hepatology*, 1995;232 (Suppl 2):17–21. Brouwer J T, Nevens F, Michielsen P, et al.; What options are left when hepatitis C does not respond to interferon? Placebo-controlled Benelux multicenter retreatment trial on ribavirin monotherapy versus combination with interferon. *J Hepatol.* 1994;212 (Suppl 1):S17. Abstract WP2/08. Chemello L, Cavalletto L, Bernardinello E, et al. Response to ribavirin, to interferon and to a combination of both in patients with chronic hepatitis C and its relation to HCV genotypes. *J Hepatol.* 1994;212 (Suppl 1):S12. Abstract GS5/29; and The effect of interferon alpha and ribavirin combination therapy in naive patients with chronic hepatitis C, *J. Hepatol.* 1995;23(Suppl.2):8–12. Reichard et al. LANCET 1998; 351;83–87 disclosed that more chronic hepatitis C patients have a sustained virologic response with a combination of interferon alpha-2b and ribavirin for 24 weeks than with only interferon alpha-2b. Reichard et al. also disclosed that interferon-alpha-2b alone is sufficient to achieve a sustained response in such patients with HCV-RNA serum values above 3 million copies/mL. However, no one has described methods using alpha interferon and ribavirin which eradicate HCV-RNA in any long-term, effective manner for antivirally naive patients having a specific HCV genotype infection.

There is a definite need for a method for treating antiviral treatment naive patients having chronic hepatitis C infection with a combination of alpha interferon and ribavirin which eradicates HCV-RNA in any long-term, effective manner.

SUMMARY OF THE INVENTION

We have discovered that if the antiviral treatment naive patient has HCV genotype 1 infection, or if the antiviral treatment naive patient has an HCV genotype 1 infection, and a viral load of greater than 2 million copies per ml of HCV-RNA by quantitative PCR, then the administration of the combination therapy of alpha interferon and ribavirin is effected for a time period of 40–50 weeks, preferably 48 weeks.

We have also discovered that if the antiviral treatment naive patient has is HCV genotype 2 or 3 infection, then the administration of the combination therapy of alpha interferon and ribavirin is effected for a time period of 20–30 weeks, preferably 24 weeks.

The present invention provides a method of treating antiviral treatment naive patients having chronic hepatitis C infection to eradicate detectable HCV-RNA comprising administering a therapeutically effective amount of ribavirin and a therapeutically effective amount of interferon-alpha for a time period of at least 20 up to 50 weeks, wherein when the antiviral treatment naive patient has a HCV genotype 1 infection, the time period of administring is about 40 to 50 weeks or wherein when the antiviral treatment naive patient has a HCV genotype 2 or 3 infection, the time period of administering is about 20 to 30 weeks.

The present invention also provides a method of treating antiviral treatment naive patients having chronic hepatitis C infection and HCV genotype 1 to eradicate detectable HCV-RNA comprising administering a therapeutically effective amount of ribavirin and a therapeutically effective amount of interferon-alpha for a time period of at least 40 to 50 weeks, such that about 17% of the patients having no detectable HCV-RNA at the end of said 20 to 30 week time period also have no detectable HCV-RNA for at least 24 weeks after the end of said administration, and such that about 29% of the patients having no detectable HCV-RNA at the end of said 40–50 week time period also have no detectable HCV-RNA for at least 24 weeks after the end of said administration.

In another embodiment, the present invention relates to a method of treating antiviral treatment naive patients having chronic hepatitis C infection and having HCV genotype 1, 4, 5 or 6 to eradicate detectable HCV-RNA comprising administering a therapeutically effective amount of ribavirin and a therapeutically effective amount of interferon-alpha for a time period of at least 40 to 50 weeks, such that about 29% of the HCV genotype 1 patients and about 39% of the HCV genotype 4, 5 or 6 patients having no detectable HCV-RNA at the end of said time period also have no detectable HCV-RNA for at least 24 weeks after the end of said administration.

Another embodiment of the invention relates to a method of treating antiviral treatment naive patients having chronic hepatitis C infection comprising administering a therapeutically effective amount of ribavirin and a therapeutically effective amount of interferon-alpha for a time period of 20 up to 50 weeks, such that about 41% of the patients having no detectable HCV-RNA at the end of said 40 to 50 week time period also have no detectable HCV-RNA for at least 24 weeks after the end of said administration; wherein the patients who have no detectable HCV-RNA at the end of a 20 to 30 week time period of said 20 to 50 week time period and also are known to be HCV-genotype 2 or 3 are treated for only 20 to 30 weeks of said 40 to 50 week period.

One aspect of the invention involves a method of treating antiviral treatment naive patients having chronic hepatitis C infection and having HCV genotype type 2 or 3 comprising administering a therapeutically effective amount of ribavirin and a therapeutically effective amount of interferon-alpha for a time period of about 20 to 30 weeks, such that about 64–65% of the patients having no detectable HCV-RNA at the end of said time period also have no detectable HCV-RNA for at least 24 weeks after the end of said administration.

Another aspect of the invention relates to a method of treating antiviral treatment naive patients having chronic hepatitis C infection and having HCV genotype type 1 and having a viral load of less than or equal to 2 million copies as measured by HCV-RNA/qPCR to eradicate detectable HCV-RNA comprising administering a therapeutically effective amount of ribavirin and a therapeutically effective amount of interferon-alpha for a time period of at least 40 to 50 weeks, such that about 33% of the patients having no detectable HCV-RNA at the end of said time period also have no detectable HCV-RNA for at least 24 weeks after the end of said administration.

Yet another aspect of the invention involves a method of treating antiviral treatment naive patients having chronic hepatitis C infection and having HCV genotype type 1 and having a viral load of greater than 2 million copies as measured by HCV-RNA/qPCR to eradicate detectable HCV-RNA comprising administering a therapeutically effective amount of ribavirin and a therapeutically effective amount of interferon-alpha for a time period of at least 40 to 50 weeks, such that about 27% of the patients having no detectable HCV-RNA at the end of said time period also have no detectable HCV-RNA for at least 24 weeks after the end of said administration.

The interferon-alpha administered is preferably selected from interferon alpha-2a, interferon alpha-2b, a consensus interferon, a purified interferon alpha product or a pegylated interferon-alpha, including a pegylated interferon-alpha-2a or a pegylated interferon alpha-2b.

More preferably, the interferon-alpha is selected from interferon alpha-2a, interferon alpha-2b, or a purified interferon alpha product and the amount of interferon-alpha administered is from 2 to 10 million IU per week on a weekly, TIW, QOD or daily basis. In a preferred embodiment, the interferon-alpha administered is interferon-alpha-2b and the amount of interferon-alpha is administered 3 million IU TIW.

Alternatively, the interferon-alpha administered is consensus interferon and the amount of interferon-alpha administered is from 1 to 20 micrograms per week on a weekly, TIW, QOD or daily basis. In another embodiment, the interferon-alpha administered is a pegylated interferon alpha-2b and the amount of interferon-alpha administered is from 0.5 to 2.0 micrograms/kilogram per week on a weekly, TIW, QOD or daily basis. Alternatively, the interferon-alpha administered is a pegylated interferon alpha-2a and the amount of interferon-alpha administered is from 20 to 250 micrograms/kilogram per week on a weekly, TIW, QOD or daily basis. The use of interferon alpha-2a or pegylated interferon alpha-2a or interferon alpha-2b or pegylated interferon alpha-2b is preferred.

During the 20–30 week and during the 40–50 week time periods, the amount of ribavirin administered is 800 to 1200 mg per day, preferably 800, 1000 or 1200 mg per day, and the amount of interferon alpha-2a or interferon alpha-2b administered is from 2 to 10 million IU per week on a weekly, TIW, QOD or daily basis, more preferably 3 million IU TIW.

DETAILED DESCRIPTION

Surprisingly, it has been found that, in the case of antiviral treatment naive patients having chronic hepatitis C infection and having HCV genotype 1, or such naive patients having HCV genotype 1 and a viral load of greater than 2 million copies per ml of HCV-RNA by quantitative PCR ("qPCR"), combination therapy with a therapeutically effective amount of ribavirin and a therapeutically effective amount of interferon alpha for a time period of at least 20 to 30 weeks results in ten times more patients having no detectable HCV-RNA in their serum at least 24 weeks after termination of therapy compared to by interferon-alpha monotherapy. When the combination therapy is extended to a time period of 40 to 50 weeks, two to three times more patients have no detectable HCV-RNA in their serum at least 24 weeks after termination of combination therapy compared to those treated with the combination therapy for 24 weeks and eight to nine times more patients have no detectable HCV-RNA in their serum at least 24 weeks after termination of combination therapy compared to those treated with interferon-alpha monotherapy for 48 weeks. See Tables 6, 14, 16 & 17, the rate of sustained virologic response found after using the combination therapy of the present invention depends upon the HCV genotype and the base line viral load as measured by HCV-RNA/qPCR as well as the treatment period of the combination therapy for HCV genotype 1. See Tables 13 & 15. The treatment period of the combination therapy for antiviral treatment naive patients having chronic HCV genotypes 4, 5 and 6 infections is the same as antiviral treatment naive patients having chronic naive patients having chronic HCV genotype 1. The treatment period of the combination therapy for antiviral treatment naive patients having HCV genotypes 2 and/or 3 is shorter, namely 20 to 30 weeks, preferably 24 weeks. See Tables 7, 13 & 15.

The term "interferon alpha" as used herein means the family of highly homologous species-specific proteins that inhibit viral replication and cellular proliferation and modulate immune response. Typical suitable interferon-alphas include, but are not limited to, recombinant interferon alpha-2b such as Intron-A interferon available from Schering Corporation, Kenilworth, N.J., recombinant interferon alpha-2a such as Roferon interferon available from Hoffmann-La Roche, Nutley, N.J., recombinant interferon alpha-2c such as Berofor alpha 2 interferon available from Boehringer Ingelheim Pharmaceutical, Inc., Ridgefield, Conn., interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain, or a consensus alpha interferon such as those described in U.S. Pat. Nos. 4,897,471 and 4,695,623 (especially Examples 7, 8 or 9 thereof) and the specific product available from Amgen, Inc., Newbury Park, Calif., or interferon alpha-n3 a mixture of natural alpha interferons made by Interferon Sciences and available from the Purdue Frederick Co., Norwalk, Conn., under the Alferon Tradename. The use of interferon alpha-2a or alpha 2b is preferred. Since interferon alpha 2b, among all interferons, has the broadest approval throughout the world for treating chronic hepatitis C infection, it is most preferred. The manufacture of interferon alpha 2b is described in U.S. Pat. No. 4,530,901.

The interferon alpha administered is selected from interferon alpha-2a, interferon alpha-2b, a consensus interferon, a purified interferon alpha product or a pegylated interferon-alpha-2a or pegylated interferon alpha-2b.

The therapeutically effective amount of interferon alpha-2a, interferon alpha-2b, or a purified interferon alpha administered in association with ribavirin is from 2 to 10 million IU per week on a weekly, TIW, QOD or daily basis.

The therapeutically effective amount of interferon-alpha-2b administered is 3 million IU TIW.

When the interferon alpha administered in association with ribavirin is consensus interferon, the therapeutically effective amount of interferon-alpha administered is from 1 to 20 micrograms per week on a weekly, TIW, QOD or daily basis.

The term "pegylated interferon alpha" as used herein means polyethylene glycol modified conjugates of interferon alpha, preferably interferon alpha-2a and alpha-2b. The preferred polyethylene-glycol-interferon alpha-2b conjugate is $PEG_{12000}$-interferon alpha-2b. The phrases "12,000 molecular weight polyethylene glycol conjugated interferon alpha" and "$PEG_{12000}$-IFN alpha" as used herein mean conjugates such as are prepared according to the methods of International Application No. WO 95/13090 and containing urethane linkages between the interferon alpha-2a or -2b amino groups and polyethylene glycol having an average molecular weight of 12000. The pegylated inteferon alpha, $PEG_{12000}$-IFN-alpha-2b is available from Schering-Plough Research Institute, Kenilworth, N.J.

The preferred $PEG_{12000}$-interferon alpha-2b is prepared by attaching a PEG polymer to the epsilon amino group of a lysine residue in the interferon alpha-2b molecule. A single $PEG_{12000}$ molecule is conjugated to free amino groups on an IFN alpha-2b molecule via a urethane linkage. This conjugate is characterized by the molecular weight of $PEG_{12000}$ attached. The $PEG_{12000}$-IFN alpha-2b conjugate is formulated as a lyophilized powder for injection. The objective of conjugation of interferon alpha with PEG is to improve the delivery of the protein by significantly prolonging its plasma half-life, and thereby provide protracted activity of interferon alpha.

Other interferon alpha conjugates can be prepared by coupling an interferon alpha to a water-soluble polymer. A non-limiting list of such polymers include other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alpha-polymer conjugates are described in U.S. Pat. No. 4,766,106, U.S. Pat. No. 4,917,888, European Patent Application No. 0 236 987, European Patent Application Nos. 0510 356, 0 593 868 and 0 809 996 (pegylated interferon alpha-2a) and International Publication No. WO 95/13090.

Pharmaceutical compositions of pegylated interferon alphasuitable for parenteral administration may be formulated with a suitable buffer, e.g., Tris-HCl, acetate or phosphate such as dibasic sodium phosphate/monobasic sodium phosphate buffer, and pharmaceutically acceptable excipients (e.g., sucrose), carriers (e.g. human plasma albumin), toxicity agents (e.g. NaCl), preservatives (e.g. thimerosol, cresol or benyl alcohol), and surfactants(e.g. tween or polysorbates) in sterile water for injection. The pegylated interferon alpha-may be stored as lyophilized powders under a refrigeration at 2°–8° C. The reconstituted aqueous solutions are stable when stored between 2° and 8° C. and used within 24 hours of reconstitution. See for example U.S. Pat. Nos. 4,492,537; 5,762,923 and 5,766,582. The reconstituted aqueous solutions may also be stored in prefilled, multi-dose syringes such as those useful for delivery of drugs such as insulin. Typical suitable syringes include systems comprising a prefilled vial attached to a pen-type syringe such as the NOVOLET Novo Pen available from Novo Nordisk, as well as prefilled, pen-type syringes which allow easy self-injection by the user. Other syringe systems include a pen-type syringe comprising a glass cartridge containing a diluent and lyophilized pegylated interferon alpha powder in a separate compartment.

When the interferon-alpha administered in association with ribavirin is a pegylated interferon alpha-2b and the amount of interferon-alpha administered is from 0.5 to 2.0 micrograms/kilogram per week on a weekly, TIW, QOD or daily basis.

When the interferon-alpha administered in association with ribavirin is a pegylated interferon alpha-2a and the amount of interferon-alpha administered is from 20 to 250 micrograms/kilogram per week on a weekly, TIW, QOD or daily basis.

Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771.

A person suffering from chronic hepatitis C infection may exhibit one or more of the following signs or symptoms:
  (a) elevated ALT,
  (b) positive test for anti-HCV antibodies,
  (c) presence of HCV as demonstrated by a positive test for HCV-RNA,
  (d) clinical stigmata of chronic liver disease,
  (e) hepatocelluar damage.

To practice the invention, the combination therapy of interferon alpha and ribavirin are administered to the patient exhibiting one of more of the above signs or symptoms in amounts sufficient to eliminate or at least alleviate one or more of the signs or symptoms. Interferon alpha formulations, including pegylated interferon alpha formulations, are not effective when administered orally, so the preferred method of administering the interferon alpha or pegylated interferon alpha formulations is parenterally, preferably by subcutaneous, IV, or IM, injection. The ribavirin is administered to the patient in association with the interferon alpha, that is, the interferon alpha dose is administered during the same period of time that the patient receives doses of ribavirin. Ribavirin may be administered orally in capsule, tablet or liquid form in association with the parenteral administration of pegylated interferon-alpha. Of course, other types of administration of both medicaments, as they become available are contemplated, such as by nasal spray, transdermally, by suppository, by sustained release dosage form, and by pulmonary inhalation. Any form of administration will work so long as the proper dosages are delivered without destroying the active ingredient.

The term "antivral treatment naive patients" in the context of the present invention means that the patients have never been treated with ribavirin or any interferon including, but not limited to an interferon-alpha.

The term "no detectable HCV-RNA" in the context of the present invention means that there is less than 100 copies of HCV-RNA per ml of serum of the patient as measured by quantitative, multi-cycle reverse transcriptase PCR methodology. HCV-RNA is preferably measured in the present invention by the methodology described below. This methodology is referred to herein as HCV-RNA/qPCR.

RNA is extracted from patient serum using a guaninidium thiocyanate- phenol-chloroform mister followed by ethanol-ammonium acetate precipitation. The precipitated RNA is centrifuged and the resulting pellet is dried in a Centrivap console (Labconco, Kansas City, Mo.). The dry pellet is then resuspended in 30 microliters of an Rnasin (Promega Corp., Madison, Wis.), dithiothritol, and diethylpyrocarbonate-treated water mixture. Samples are kept at or below −20° C. (preferably below −70° C.) until RNA reverse transcription (RT) and PCR.

In order to convert the entire RNA sequence into cDNA in the RT reaction, random hexadeoxyribonucleotides (Pharmacia Biotech, Piscataway, N.J.) are used as primers for the first strand cDNA synthesis. Two aliquots of 3 microliters of resuspended sample is added to 3 microliters of 100 ng/$\mu$l random primers and denatured at 70° C., then reverse transcribed at 40° C. for one hour using M-MLV reverse transcriptase (USB, Cleveland, Ohio.) in standard buffer containing 5 mM $MgCl_2$. The final RT reaction volume is 26 $\mu$l. The PCR is started immediately following the reverse transcription.

A modified version of the PCR method is performed using heat-stable Taq polymerase to amplify the cDNA. Seventy-five microliters of PCR mix is added to the entire RT reaction volume (26 $\mu$l) to a final $MgCl_2$ concentration of 1.5 mM in a total volume of 101 $\mu$l. Each 101 $\mu$l sample is then split into 50.5 $\mu$l, and a layer of mineral oil is placed on top to prevent evaporation.

The PCR cycle consists of annealing for 90 sec., extension for 90 sec., and denaturation for 90 sec., at 55°×, 74° C. and 94° C., respectively. Thermocycling samples is submitted to a final 74° C. extension for 10 minutes. Four different cycle sets are used. By loading the sample in duplicate, and splitting these samples evenly after RT, there are four tubes from one sample. Each of the four tubes is given a different cycle number, enhancing sensitivity and accuracy in the quantitation process. The thermocycling efficiency will be assessed by satisfactory amplification of known copy number RNA standards included in each set of 60 tubes. Two primer sets are used for the amplification, both from the 5' untranslated region of the HCV genome. Both of these primer sets are highly conserved and detect all known subtypes of HCV. Primer set 1: upstream 5'-GTG GTC TGC GGA ACC GGT GAG T-3' (SEQ ID NO:1, downstream-5'-TGC ACG GTC TAC GAG ACC TC-3' (SEQ ID NO:2) which produced a 190 bp product. Primer set 2: upstream 5'-CTG TGA GGA ACT ACT GTC TTC-3' (SEQ ID NO:3), downstream 5'-CCC TAT CAG GCA GTA CCA CAA-3' (SEQ ID NO:4) which produced a 256 bp product.

The amplified cDNA is then electrophorised in 3% agarose gel and transferred to nylon membrane. The target DNA is detected by Southern blotting and immunostaining using a nonradioactive digoxigenin-labeled DNA probe. These procedures are performed using automated instruments for PCR thermocycling, agarose gel electrophoresis, vacuum-transfer Southern blot, hybridization, and immunostaining. Each membrane contains known copy number serially diluted standards which are used to construct standard curves for quantitative measurement of the specimen bands. Originally standard curves are made from carefully diluted HCV-RNA from transcribed clones. Radioactive incorporation studies, gel electrophoresis, and OD 260 are performed on the transcripts to determine that they are of the expected length. After the production of the RNA transcripts quantitated clone standards "pooled" standards are generated which better represent the heterogeneous nature of HCV, one would encounter in natural infection. These pools are made by combining large amounts of serum or plasma from known infected individuals. The serum/plasma pools are calibrated with PCR, against the clone transcripts and then diluted in the known PCR-negative fluids. Finally, the higher copy number samples of the pools are checked against the cDNA Quantiplex nucleic acid detection system from Chiron Inc. (Emeryville, Calif.). These "double quantitated" pools are aliquoted and saved at −70° C. Dilutions of 5,000,000, 1,000,000, 500,000, 100,000, 10,000, and 1000 copies/ml are used in each experiment.

Each Southern blot membrane is scanned into a computer using an automated scanner/densitometer, at intervals during development to determine when the standard curve is most linear. The resultant electronic images are then measured for band area and mean band density. All of the reading are standardized to integrated band density and compared to the standard curve to obtain a numerical value of viral copy number for each band.

The term "sustained virologic response" as used in the context of the present invention means that there is no detectable HCV-RNA in the serum of patients treated in accordance with the present invention for at least 24 weeks after the end of the combined therapy treatment. Preferably, the period of sustained virologic response is at least one year—or longer—after the end of treatment.

The following clinical protocols were performed:

Study 1:

Overall Design and Plan of the Study

This was a prospective, multicenter, randomized, double-blind, parallel-group. The study compared treatment with INTRON® A plus ribavirin to treatment with INTRON® A plus placebo for 24 or 48 weeks in antiviral treatment naive patients with compensated chronic hepatitis C who had no prior treatment with any interferon including but not limited to alpha interferon (INTRON® A, Roferon®-A, consensus interferon, or Wellferon®) therapy and who also had no prior treatment with ribavirin. Patients who had prior treatment for hepatitis with any other antiviral or immunomodulatory drug within the previous 2 years were also excluded from this study. Eligible patients had chronic hepatitis C confirmed by positive serum HCV-RNA, liver biopsy, and laboratory tests.

Patients were randomized to treatment with either INTRON® A plus ribavirin or INTRON® A plus placebo. The dose of INTRON® A was 3 million IU SC TIW; the dose of ribavirin was 1000 or 1200 mg PO daily (based on weight) in two divided doses. Treatment group assignments were made in equal ratios by a Central Randomization Center. The randomization procedure was designed to attempt to balance the treatment groups, within and across sites, with respect to presence or absence of cirrhosis in the pretreatment liver biopsy, serum HCV-RNA/qPCR level, and HCV genotype.

Study treatment was administered for 24 or 48 weeks. The total course of the study was 48 or 72 weeks to determine long-term effect of treatment. Duration of treatment was assigned at the time of randomization.

During treatment and posttreatment follow-up, biochemical (ALT), virological (HCV-RNA), and histological (liver biopsy) examinations were used to assess the nature and duration of response to study treatment. The primary efficacy variable was the overall response defined as loss of serum HCVRNA/qPCR (<100 copies/mL) as measured at 24 weeks following the end of therapy. In addition, a decrease in hepatic inflammation, an improvement in posttreatment liverbiopsyas measured by the Knodell Histology Activity index (HAI) and normalization of ALT were also examined as a secondary efficacy endpoints. The safety of the study treatments was assessed by monitoring selected laboratory parameters and by also recording and evaluating the occurrence of any adverse events.

Treatment Regimens

There were four study treatment regimens:

1. INTRON® A 3 million IU SC TIW plus ribavirin 1000 or 1200 mg/day PO in two divided doses for 24 weeks; or
2. INTRON® A 3 million IU SC TIW plus placebo matching ribavirin PO in two divided doses for 24 weeks; or
3. INTRONS A 3 million IU SC TIW plus ribavirin 1000 or 1200 mg/day PO in two divided doses for 48 weeks; or
4. INTRON® A 3 million IU SC TIW plus placebo matching ribavirin PO in two divided doses for 48 weeks.

Study treatments 1 and 2 were administered for 24 weeks; study treatments 3 and 4 were administered for 48 weeks. The standard INTRON® A (interferon alpha-2b, recombinant) regimen for hepatitis C was administered as a fixed dose of 3 million IU TIW. Each patient received instructions regarding the preparation and subcutaneous administration of INTRON® A. Ribavirin was administered twice daily, morning and evening. The dose was determined by the patient's body weight at the Entry visit. Patients weighing $\leq 75$ kg received 1000 mg daily as two 200 mg capsules in the morning and three 200 mg capsules in the evening. Patients weighing >75 kg received 1200 mg daily as three 200 mg capsules morning and evening.

The randomization procedure was designed to balance the groups with respect to the following Baseline characteristics:

pretreatment liver histology (cirrhosis or no cirrhosis);
serum HCV-RNA/qPCR status (HCV-RNA/qPCR $\leq 2,000,000$ or HCV-RNA/qPCR >2,000,000 copies/mL); and
HCV Genotype (1 or other). Patients with mixed genotypes (which include Type 1) will be classified as Type 1 for purposes of balancing.

Efficacy

The primary efficacy objective was comparison of the treatment groups 1 and 2 and 3 and 4 with respect to the sustained virologic response rate defined as loss of (detectable) serum HCV-RNA/qPCR measured at 24 weeks following the end of therapy to an undetectable level or to a level <100 copies/mL. The following secondary efficacy Endpoints were also examined:

The secondary efficacy Endpoints:

proportions of patients with normalization of ALT at 24 weeks of follow-up;
proportions of patients with improvement in biopsy (Categories I+II+III combined scores);
changes from Baseline in the biopsy scores (Categories I+II+III combined scores);
response rates at Endpoint of treatment based on HCV-RNA/qPCR;
proportion of patients with normalization of ALT at Endpoint of treatment.
response rates at 24 weeks of follow-up based on HCV-RNA/qPCR.

Virology: Entry Status and Change from Entry

Serum HCV-RNA/qPCR testing was performed by a central laboratory. A positive HCV-RNA assay result was required at Baseline; only patients positive for HCV-RNA were eligible to participate. Repeat assays were scheduled at Weeks 4, 12, 24, and if the patient was in the 48 week treatment groups at weeks 36 and 48. All patients had repeat assays scheduled for Follow-up Weeks 12 and 24.

Response was assessed as defined below:

| | |
|---|---|
| Responder: | A patient was classified as a responder at a given time point if HCV-RNA/qPCR was negative (<100 copies per mL) at that time point. |
| Sustained Responder: | A patient was classified as a sustained responder if the patient was a responder at 24 weeks of follow-up. Note that patients who do not meet these criteria, including patients who discontinued before the required HCV-RNA/qPCR evaluations were obtained, were classified as non-responders. |
| Overall Responder: | Based on both serum HCV-RNA/qPCR and change in liver histology as evaluated by the Knodell HAI Inflammation Score. A patient was classified as an overall responder to treatment if he/she was a sustained responder and his/her Post treatment Knodell HAI inflammation score (sum of categories I+II+III) improved by 2 or more units relative to the Pretreatment score. |

Liver Histology

Liver biopsy was required within the six months preceding patient enrollment and at Follow-up Week 24 for all patients. Evaluation of the biopsies was performed by a single pathologist using the Knodell Histology Activity Score. The central pathologist was blinded with respect to patient identification, treatment group, and the time the biopsy was obtained relative to treatment(Pre- or Posttreatment). Efficacy of study treatments was assessed by comparing the degree of inflammatory activity observed at Baseline with that present at Follow-up Week 24.

RESULTS

Nine hundred-twelve patients were enrolled at 42 US centers and randomized to treatment with either INTRON® A plus ribavirin (N=228) or INTRON® A plus placebo (N=23) for 24 weeks or treatment with either INTRON A plus ribavirin ("I+R") (N=228) or INTRON A plus placebo ("I+P") (N=225) for 48 weeks.

Overall, 81% (734/912) of patients completed treatment and 24 weeks of follow-up. Eighty-nine percent (203/228) of patients in the 24 week I+R group, 90% (207/231) of patients in the 24 week I+P group, 70% (159/228) of patients in the 48 week I+R group, and 73% (165/225) of patients in the 48 week I+P group completed the study.

Twenty percent (178/912) of patients discontinued during treatment: 11% (25/228) in the 24 week I+R group, 10% (24/231) in the 24 week I+P group, 30% (69/228) in the 48 week I+R group, and 27% (60/225) in the 48 week I+P group. An adverse event was the most frequent reason a patient discontinued treatment in all groups (8% [19/228] with 24 weeks of I+R, 9% [20/231] with 24 weeks of I+P, 20% [45/228] with 48 weeks of I+R, and 14% [32/225] with 48 weeks of I+P.

At least 96% of patients who completed treatment and entered follow-up completed the study. Only 2 patients in the I+R 24 week group, 8 patients in the 24 week I+P group, 7 patients in the I+R 48 week group, and 4 patients in the 48 week I+P group discontinued during follow-up.

The patient's weight and their baseline disease characteristics (HCV genotype and initial viral load) for all patients in Study 1 is given in Table 1 below. HCV genotypes were done on the patient serum samples subjected to HCV-RNA/qPCR testing.

TABLE 1

Body Weight and Baseline Disease Characteristics for Study 1 Patients

| Weight | I + R[1] 24 Wks (N = 228) | I + P[2] 24 Wks (N = 231) | I + R[1] 48 Wks (N = 228) | I + P[2] 48 wks (N = 225) |
|---|---|---|---|---|
| >75 kg | 148 (65%) | 157 (68%) | 133 (58%) | 153 (685) |
| <75 kg | 80 (35%) | 74 (32%) | 95 (42%) | 72 (32%) |
| HCV Genotype[3] | | | | |
| 1 | 164 (72%) | 167 (72%) | 166 (73%) | 162 (72%) |
| 2 | 29 (13%) | 38 (17%) | 37 (16%) | 43 (19%) |
| 3 | 28 (12%) | 24 (10%) | 23 (10%) | 19 (8%) |
| 4 | 6 (3%) | 2 (0.9%) | 1 (0.4%) | 1 (0.4%) |
| 5 | 0 | 0 | 1 (0.4%) | 0 |
| 6 | 1 (0.4%) | 0 | 0 | 0 |
| HCV-RNA/qPCR | | | | |
| (copies/$_{mL}$), | | | | |
| Geometric Mean | 3,070,019 | 2,767,469 | 2,922,925 | 2,819,324 |
| ≦2 million copies/mL | 62 (27%) | 74 (32%) | 76 (33%) | 63 (28%) |
| >2 million copies/mL | 166 (73%) | 157 (68%) | 152 (67%) | 162 (72%) |

[1]I + R is Intron A + Ribavirin
[2]I + P is Intron A + Placebo
[3]Sub-genotypes are classified under their respective genotype.

All discussions of efficacy and safety in this report are based on data for the all-treated groups.

Efficacy

The objectives of this study were to compare INTRON® A plus ribavirin with INTRON® A plus placebo with respect to the overall response rate and the virologic response rate (based on HCV-RNA (qPCR) for 24 and 48 weeks. The primary efficacy variable for the study is the overall response rate.

The conclusions from this regarding efficacy are as follows:

The combination therapy of INTRON A plus ribavirin administered for 48 weeks increased by 2 to 3-fold the efficacy of INTRON A monotherapy for the treatment of chronic hepatitis C in antiviral treatment naive patients. Forty-eight weeks of the combination therapy of INTRON A plus ribavirin increased the response rate at the End of Treatment and decreased the rate of relapse, which resulted in a better sustained virologic response rate than for 48 weeks of INTRON A+Placebo. This enhancement of efficacy included all aspects of the disease and resulted in:
Sustained eradication of detectable HCV-RNA;
Improvement in hepatic inflammation;
Normalization of ALT;
Improvement in Knodell HAI inflammation score.

Sustained loss of serum HCV-RNA correlated with improvement in or resolution of hepatic inflammation. Results demonstrated correlation between sustained virologic response, improvement in hepatic inflammation, normalization of ALT and improvement in HQL.

The End of Follow-up overall response rate is a composite of the loss of serum HCV-RNA(qPCR) and change in liver histology at end of follow-up (24 weeks following the end of treatment). A patient was classified as an overall responder if HCV-RNA(PCR) was negative at the 24 week posttreatment evaluation and the posttreatment Knodell HAI inflammation score (sum of categories I+II+III) had improved if the posttreatment value had decreased by 2 or more units relative to the pretreatment score. The percent of sustained virologic responders by time to first negative HCV-RNA, the End of Follow-up (sustained) virologic response, histologic response, and overall response rates are summarized in Tables 2, 3, 4 and 5.

End of Follow-up HCV-RNA Sustained Virologic Response: Sustained Loss of HCV-RNA 24 Weeks Following the End of Treatment The proportion of patients with eradication of HCV-RNA in the serum 24 weeks following the End of Treatment was two-threefold greater (41% v. 16%) in the group of patients treated with the combination of INTRON® A plus ribavirin compared to those receiving INTRON® A plus placebo.

The increased length of the combination therapy had the greatest effect on relapse rates. At 24 weeks following End of the Treatment, the relapse rates for 48 weeks of the combination therapy and for 48 weeks of Intron A plus placebo were the same (12%). Longer treatment with the combination therapy (48 weeks) and decreased relapse rates resulted in the highest sustained virologic response rates. Sustained virologic response rates were also significantly higher with 48 weeks of the combination therapy compared to 24 weeks of the combination therapy (38% vs 31%, p value=0.053.)

Extending the combination therapy from 24 to 48 weeks substantially increased sustained virologic responses in patients who first became HCV-RNA negative at Weeks 12 and 24. The majority of patients who became sustained virologic responders were HCV-RNA negative by Week 4. As summarized in Table 2, the sustained virologic response was observed for 81% (35/44) of the patients on 24 weeks of combination therapy (I+R) at Week 4 of the 24 week treatment and for 81% (36/45) of the patients on the 48 weeks of combination therapy at Week 4 of the 48 week treatment. Note that substantial portions of these patients on the 24 and 48 week combination therapy who responded for the first time at Week 12 became sustained virologic responders. In 42% of these patients in the 24 week combination therapy group and 63% of these patients in the 48 week combination therapy group, these responses were sustained. Furthermore, 44% of the patients in the 48 week combination therapy treatment group who first became HCV-RNA negative at Week 24 achieved a sustained virologic response. None of the responses that occurred after Week 24 became sustained responders in any treatment group.

The number of first time responders at Weeks 12 and 24 who become sustained virologic responders 24 weeks after end of treatment were greatest for the patients who received 48 weeks of combination therapy. (See Table 2 below.)

TABLE 2

Percent of Sustained Virologic Responders by Time to First No Detectable HCV-RNA Levels for Study 1

| Time to First No-Detectable HCV-RNA (Weeks) | Intron A + Ribavirin | | Intron A + Placebo | |
|---|---|---|---|---|
| | 24 weeks | 48 weeks | 24 weeks | 48 weeks |
| 4 | 81% (35/43) | 80% (36/45) | 48% (10/21) | 70% (14/20) |
| 12 | 42% (30/72) | 63% (40/63) | 9% (3/32) | 35% (11/31) |
| 24 | 46% (5/11) | 44% (11/25) | 0% (0/22) | 22% (4/18) |

Table 3 summarizes the End of Follow-up patient response as indicated by serum HCV-RNA.

TABLE 3

End of Follow-up Serum HCV-RNA: Proportion of Patients with Eradication of HCV-RNA at 24 Weeks Following the End of Treatment. (EOT)

| Patient Response Status All Treated 95% Confidence Interval | INTRON A + Ribavirin | | INTRON A + Placebo | | Value[1] B vs D | P-Value[1] A vs D |
|---|---|---|---|---|---|---|
| | A 24 weeks | B 48 weeks | C 24 weeks | D 48 weeks | | |
| At EOT | | | | | | |
| Negative | 121 (53%) | 115 (50%) | 66 (24%) | 54 (24%) | <0.001 | <0.001 |
| Positive | 107 (47%) | 113 (50%) | 165 (71%) | 171 (76%) | | |
| At End of Follow-up | | | | | | |
| Sustained Responders | 70 (31%) | 87 (38%) | 13 (6%) | 29 (13%) | <0.001 | <0.001 |
| Relapser | 54 (24%) | 28 (12%) | 53 (23%) | 26 (12%) | | |
| Non Responder | 104 (46%) | 113 (50%) | 165 (71%) | 170 (76%) | | |

[1]Fisher's Exact Test for End of Treatments P Value A vs B is 0.639; p value for A vs C <0.001.
[2]Logistic Regression for End of Follow-Up Comparisons; P Value A vs B is 0.053; p value for A vs C < 0.001.

Combination therapy significantly increased the virologic response at the end of treatment compared to INTRON A monotherapy. See Table 3. The p values for comparison of the combination therapy for 48 weeks with INTRON A monotherapy for 48 weeks and the comparisons of 24 weeks of combination therapy with 24 and 48 weeks of INTRON A monotherapy are each <0.001. Extending the combination therapy from 24 to 48 weeks decreased the relapse rate by 50% (24% to 12%) thereby making the 48 week combination therapy more effective than the 24 week combination (p=0.053).

Pre- and Posttreatment biopsies were available for 79% (179/228) and 69% (157/228) of the patients treated with INTRON® A plus ribavirin for 24 and 48 weeks respectively and for 76% (176/231) and 70% (158/225) of those patients who received INTRON® A plus placebo for 24 and 48 weeks, respectively. Table 4 summarizes the effect of treatment on hepatic inflammation for patients with both pre- and posttreatment liver biopsy results. As with the sustained loss of HCV-RNA replication, the proportion of patients with improvement in liver inflammation was significantly greater (p<0.001) in patients receiving combination therapy compared to those receiving INTRON® A monotherapy for 48 weeks.

Eradication of detectable HCV-RNA was highly correlated with normalization of serum ALT. Two to three-fold more patients were ALT normal with the combination therapy compared to INTRON A monotherapy at the End of Follow-Up. Among patients who had sustained normalized ALT, a higher proportion of 48 week combination therapy patients were sustained virologic responders compared with patients who received 24 weeks of combination therapy and 24 weeks or 48 weeks of INTRON A monotherapy.

TABLE 4

End of Follow-up Liver Histology: Improvement In Liver Histology 24 Weeks Following the End of Treatment Based on the Knodell HAI (I + II + III) Score.

| | Number (%) of Patients[b] | | | | |
|---|---|---|---|---|---|
| | INTRON A + Ribavirin | | INTRON A + Placebo | | |
| Patient Status | A 24 weeks (N = 179)[a] | B 48 weeks (N = 157)[a] | C 24 weeks (N +176)[a] | D 48 weeks (N = 158) | P Value[c] |
| Improved Biopsy[d] | 102 (57%) | 96 (61%) | 77 (44%) | 65 (41%) | <0.001 |

[a]N = Number of Patients with paired biopsy samples.
[b]Patients with both pre and posttreatment biopsy.
[c]Fisher's Exact test.
[d]Change from pretreatment to posttreatment in the Knodell Histological Index (HAI) score (sum of I + II + III) categorized as a decrease of 2 or more from pretreatment.

Overall Response

When the study was designed, it was recognized that because liver biopsy is an invasive procedure that it would be unlikely that posttreatment liver biopsies would be obtained for all patients. Therefore, the protocol and statistical analysis plan specified that the analysis for overall response would be based on data for all treated patients and will be estimated by a maximum likelihood method (MLE) for patients whose overall response status could not be determined, ie, patients with negative HCV-RNA and missing (posttreatment) biopsy evaluations. The protocol also specified that an additional analysis would be performed on patients with both pretreatment and posttreatment biopsy results (ie, patients with complete data). The overall response is a composite of sustained loss of detectable HCV-RNA and improvement in liver histology at End of Follow-Up. Overall response is summarized in Table 5 based on the following analyses:

maximum likelihood estimate (MLE);
patients with complete data (results for both pre- and posttreatment biopsy);
patients with missing data (either or both HCV/biopsy) treated as failures.

TABLE 5

Overall Response Rate.

| Data Analyzed | INTRON A + Ribavirin | | INTRON A + Placebo | | p value[b] B vs D |
|---|---|---|---|---|---|
| | A 24 weeks | B 48 weeks | C 24 weeks | D 48 weeks | |
| Maximum likelihood estimate[a] | 26% | 35% | 5% | 9% | <0.001 |
| Patients with complete data[c] | 29% (52/179) | 41% (64/157) | 5% (8/170) | 11% (18/158) | <0.001 |
| Treat missing as failures[d] | 23% (52/228) | 28% (64/228) | 28% (64/228) | 8% (18/225) | <0.001 |

[a]MLE based on logistic regression. Logistic regression analysis of patients with complete biopsy data. The p value for A vs D is <0.001 and for A vs B is 0.096.
[b]Fisher's exact test.
[c]Complete data pre and posttreatment biopsy results. Logistic regression analysis.
[d]Patients who had either virology or biopsy data missing or both were counted as non-responders.

As would be anticipated from individual results for effect of treatment on eradication of HCV-RNA at end of follow-up and improvement in hepatic inflammation, the overall response rate in the INTRON® A plus ribavirin 48 week treatment group was significantly greater (<0.001), than that observed in the INTRON® A plus placebo 48 week treatment group. There was a statistically significant improvement in the overall response with the 48 week combination therapy treatment compared to 48 weeks of INTRON A monotherapy treatment as measured by MLE and complete biopsy. The overall response rates for 24 and 48 weeks of combination therapy treatment was significantly higher than with 24 and 48 weeks of INTRON A monotherapy, respectively.

Logistic regression analysis was done on all baseline demographic variables and disease characteristics. The only baseline statistically significant patient and disease characteristics predictive of End of Follow-up sustained response were genotype other than 1 and viral load $\leq 2$ million.

For number of viral copies ($\leq 2$ million, >2 million), the difference was statistically significant in favor of higher response rates in patients with $\leq 2$ million copies (Table 6).

When genotype and baseline virus load are combined, a hierarchy of response is observed. Those patients with genotype other than 1 and baseline virus load $\leq 2$ million copies who received 24 and 48 weeks of combination therapy had the best End of Follow-up response; the sustained virologic response for those patients with genotype 1 and >2 million copies who had 48 weeks of the INTRON A plus ribavirin combination therapy was two times better than those same type patients who had the combination therapy for only 24 weeks. (See Table 6)

TABLE 6

Disease Characteristics vs Sustained Response: All-Treated Patients.

| | Number (%) of Patients | | | |
|---|---|---|---|---|
| Disease | INTRON A + Ribavirin | | INTRON A + Placebo | |
| Characteristic[a] | 24 weeks | 48 weeks | 24 weeks | 48 weeks |
| HCV-RNA/viral load | | | | |
| $\leq 2$ million copies/ml | 42% (26/62) | 43% (33/76) | 9% (7/74) | 29% (18/63) |
| >2 million copies/mL | 27% (44/166) | 36% (54/152) | 4% (6/157) | 7% (11/162) |
| HCV Genotype | | | | |
| 1 | 16% (26/164) | 28% (46/166) | 2% (3/167) | 7& (11/162) |
| Other Genotypes | 69% (44/64) | 66% (41/62) | 16% (20/64) | 29% (18/63) |
| Genotype/Baseline HCV-RNA | | | | |
| Other Genotypes $\leq 2$ million copies/ml | 88% (14/16) | 71% (15/21) | 25% (5/20) | 50% (10/20) |

TABLE 6-continued

Disease Characteristics vs Sustained Response: All-Treated Patients.

| | Number (%) of Patients | | | |
|---|---|---|---|---|
| Disease | INTRON A + Ribavirin | | INTRON A + Placebo | |
| Characteristic[a] | 24 weeks | 48 weeks | 24 weeks | 48 weeks |
| Other Genotypes >2 million copies/ml | 63% (30/48) | 63% (26/41) | 11% (5/44) | 19% (8/43) |
| Genotype 1, $\leq$2 million copies/ml | 26% (12/46) | 33% (18/55) | 4% (2/54) | 19 % (8/43) |
| Genotype 1, >2 million copies/ml | 12% (14/118) | 25% (28/111) | 1% (1/113) | 3% (3/119) |

[a]At entry, patients were stratified by number of HCV viral copies ($\leq$2 million, >2 million), genotype (1 or other), and cirrhosis (present or absent) as measured by HCV-RNA/of PCR.

TABLE 7

Sustained Virologic Response Rates (%) by HCV Genotype

| | INTRON A + Ribavirin | | INTRON A + Placebo | |
|---|---|---|---|---|
| Genotype | 24 weeks | 48 weeks | 24 weeks | 48 weeks |
| 1 | 16% (27/165) | 28% (46/166) | 21% (4/168) | 7% (11/162) |
| 2 | 83% (25/30) | 68% (25/37) | 18% (7/38) | 35% (15/43 |
| 3 | 57% (16/28) | 65% (15/23) | 8% (2/24) | 16% (3/19) |
| 4–6 | 40% (2/5) | 50% (1/2) | 0 | 0 |

7 illustrates that the sustained virologic response rates for patients of each genotype with 48 weeks of the combination therapy were greater than those treated with Intron A plus placebo for 24 and 48 weeks. With the exception of HCV-genotype 2 patients, extending the duration of the combination therapy increased the proportion of patients with sustained virologic responses. But see Table 15 for combined virologic responses for Studies 1 & 2). Logistic regression analysis of sustained virologic response demonstrated that, in addition to treatment group, HCV genotype other than 1 and $\leq$2 million copies of baseline HCV virus/mL were significant predictors of sustained virologic response (p value $\leq$0.0111). Most notably, treatment with the combination therapy for 48 weeks improved the sustained virologic response rates for patients expected to have the lowest response rates, namely, those patients with HCV-genotype 1 and greater than 2 million copies of HCV virus/mL. These patients had sustained virologic response rates which were two fold greater than those who had 24 weeks of treatment with the combination therapy. Significantly the sustained virologic response for HCV-genotype 1 patients who received 48 weeks of combination therapy was 1.75 times greater than that for those who received 24 weeks of combination therapy.

Study 2:

By basically the same methodology as described above in Study 1, Study 2 was also conducted in 43 international sites (832 patients) using the following three treatment regimens:

The results are summarized below:
1. INTRON® A 3 million IU SC TIW plus ribavirin 1000 or 1200 mg/day PO in two divided doses for 24 weeks; or
2. INTRON® A 3 million IU SC TIW plus ribavirin 1000 or 1200 mg/day PO in two divided doses for 48 weeks; or
3. INTRON® A 3 million IU SC TIW plus placebo matching ribavirin PO in two divided doses for 48 weeks Efficacy The primary efficacy objective is sustained virologic response as defined by the loss of detectable serum HCV-RNA(qPCR) measured at End of Follow-up (24 weeks following the end of treatment). A patient was classified as an overall responder if HCV-RNA(PCR) was negative at the 24 week posttreatment evaluation and the posttreatment Knodell HAI inflammation score (sum of categories I+II+III) had improved (decreased) by 2 or more units relative to the pretreatment score. The percent of sustained virologic responders by time to first negative HCV-RNA, the End of Follow-up virologic response, histologic response, and overall response rates are summarized in Tables 9, 10, 11 and 12.

Patient body weight and their baseline disease characteristics (HCV genotype and initial viral load) for all patients in Study 2 is given in Table 8 below.

TABLE 8

Body Weight and Baseline Disease Characteristics for Study 2 Patients

| | INTRON A + Ribavirin | | INTRON A + Placebo |
|---|---|---|---|
| Body Weight | 24 weeks | 48 weeks | 48 weeks |
| >75 kg | 116 (42%) | 129 (47%) | 122 (44%) |
| $\leq$75 kg | 181 (58%) | 148 (53%) | 156 (56%) |
| HCV Genotype | | | |
| 1 | 161 (58%) | 159 (57%) | 168 (60%) |
| 2 | 27 (10%) | 23 (8%) | 21 (8%) |
| 3 | 73 (26%) | 74 (27%) | 79 (28%) |
| 4 | 12 (4%) | 16 (6%) | 9 (3%) |
| 5 | 1 (0.4%) | 5 (2%) | 1 (0.4%) |
| 6 | 3 (1%) | 0 | 0 |
| HCV-RNA/of PCR (copies/ml) | | | |
| mean geometric | 2,229,797 | 2,064,959 | 2,351,824 |
| $\leq$2 million copies/mL | 108 (39%) | 115 (42%) | 95 (34%) |
| >2 million copies/mL | 169 (61%) | 162 (59%) | 183 (66%) |

TABLE 9

Percent of Sustained Virologic Responders by
Time to First No Detectable HCV-RNA Levels for Study 2

| Time to First No-Detectable HCV | Intron A + Ribavirin | | Intron A + Placebo |
|---|---|---|---|
| RNA (Weeks) | 24 weeks | 48 weeks | 48 weeks |
| 4 | 84% (57/68) | 83% (58/70) | 72% (33/46) |
| 12 | 47% (36/77) | 69% (51/74) | 34% (18/53) |
| 24 | 12% (3/26) | 45% (9/20) | 10% (2/21) |

As summarized in Table 9, the majority of patients who became sustained virologic responders had negative HCV-RNA levels by Week 4 of treatment. However, substantial proportions of patients in the 24 and 48 week combination therapy treatment groups who were HCV-RNA positive at Week 4 responded for the first time at Week 12; 47% of those in the 24 Week treatment group and 69% of those in the 48 Week treatment group became sustained responders. Importantly, 45% (9/20) of the patients in the 48 Week combination therapy treatment group who first became negative at Week 24 became sustained virologic responders. None of the responses that occurred after Week 24 became sustained in any of the three treatment groups.

End of Follow-up HCV-RNA Response: Sustained Loss of HCV-RNA 24 Weeks Following the End of Treatment The proportion of patients with eradication of HCV-RNA in the serum 24 weeks following the end of the combination therapy treatment was significantly greater in patients treated with the combination therapy of INTRON® A plus ribavirin compared to those receiving INTRON® A monotherapy. Table 10 summarizes the End of Follow-up patient response as indicated by serum HCV-RNA.

TABLE 10

End of Follow-up Serum HCV-RNA: Proportion of Patients with Eradication of HCV-RNA at 24 Weeks Following the End of Treatment. (EOT) and End of Follow-Up (EOFU).

| | Number (%) of Patients | | | |
|---|---|---|---|---|
| | INTRON A + Ribavirin | | INTRON A + Placebo | |
| | A<br>24 weeks<br>(N = 277) | B<br>48 weeks<br>(N = 277) | C<br>48 weeks<br>(N = 278) | p value<br>B vs C$^1$ |
| EOT$^2$ | | | | |
| Negative | 57% (157) | 52% (145) | 33% (93) | <0.001 |
| Positive | 42% (120) | 42% (132) | 65% (185) | |
| EOFU$^3$ | | | | |
| Sustained | 35% (96) | 43% (118) | 19% (53) | <0.001 |
| Relapse | 23% (23) | 10% (27) | 15% (41) | |
| Non Responders | 42% (42) | 48% (132) | 66% (184) | |

$^1$Fisher's Exact Test for EOT comparisons; logistic regression for EOFU.
$^2$EOT = End of Treatment. P value for A vs C = <0.001 and for A vs B is 0.348.
$^3$EOFU = End of Follow-Up. P value for A vs C = <0.001 and for A vs B is 0.055.

Table 10 illustrates that (1) the 24 and 48 week combination therapies significantly increased the sustained virologic response at the end of treatment compared to that for the Intron A monotherapy (p values are both <0.001) and (2) the increasing the length of the Combination Therapy from 24 to 48 weeks had the greatest effect on relapse rates (10% for 48 weeks vs 23% for 24 weeks, p value is 0.055.)

End of Follow-up Liver Histology: Improvement in Liver Histology 24 Weeks Following the End of Treatment Based on Knodell Histological Activity Index (HAI) Scores (I+II+III)

Pre- and Posttreatment biopsies were available for 74% (204/277) and 60% (167/277) of the patients treated with INTRON® A plus ribavirin for 24 and 48 weeks, respectively, and for 69% (191/278) of those patients who received INTRON® A plus placebo. Table 11 summarizes the effect of treatment on hepatic inflammation for patients with both pre-and posttreatment liver biopsy results. As with the sustained loss of HCV-RNA replication, the proportion of patients with improvement in liver inflammation was significantly greater (p<0.001) in patients receiving combination therapy for 48 weeks compared to those receiving INTRON® A monotherapy for 48 weeks. Extending the combination therapy from 24 to 48 weeks also significantly increased the proportion of patients who had improvement in hepatic inflammation (p value=0.046).

TABLE 11

End of Follow-up Liver Histology: Improvement in Liver Histology 24 Weeks Following the End of Treatment Based on the Knodell HAI (I + II + III) Score.

| | Number (%) of patients$^b$ | | | |
|---|---|---|---|---|
| | INTRON A + Ribavirin | | INTRON A + Placebo | |
| Patient Status | A<br>24 weeks<br>(N = 204)$^a$ | B<br>48 weeks<br>(N = 167)$^a$ | C<br>48 weeks<br>(N = 191)$^a$ | p value$^c$<br>B vs C |
| Improved Biopsy$^d$ | 53% (107) | 63% (105) | 39% (74) | <0.001 |

$^a$Number of patients wit paired biopsies.
$^b$Patients with both pre-and posttreatment biopsy.
$^c$Fisher's Exact test. P value for A vs C = 0.007 and A for A vs B is 0.046.
$^d$Change from pretreatment to posttreatment in the Knodell Histological Index (HAI) score (sum of I + II + III) categorized as a decrease of 2 or more from pretreatment.

Overall Response

The overall reponse is summarized in Tbale 12 based on the following analyses:
- maximum likelihood estimate (MLE)
- patients with complete data (results for both pre- and posttreatment biopsy);
- patients with missing data (either or both HCV-RNA/biopsy) treated as failures.

TABLE 12

Overall Response Rate.

| | INTRON A + Ribavirin | | INTRON A + Placebo |
|---|---|---|---|
| Data Analyzed | A<br>24 weeks | B<br>48 weeks | C<br>48 weeks |
| ML Estimate | 28% | 37% | 17% |
| Patients with Complete Biopsy Data$^c$ | 30% (62/204) | 41% (68/167) | 17% (32/191) |
| Treat Missing as Failures$^d$ | 22% (62/277) | 24% (68/277) | 12% (32/278) |

$^a$MIE based on logistic regression. P value for B vs C = <0.001 and for A vs C = <0.002 and for A vs B is 0.043.
$^b$Fisher's Exact test.
$^c$Complete data = pre and posttreatment biopsy results. P value for B vs C is <0.001, for A vs C is <0.005 and for A vs B is 0.032.
$^d$Patients who had either virology or biopsy data missing or both were counted as failures.

As would be anticipated from individual results for effect of treatment on eradication of HCV-RNA at End of Follow-up and improvement in hepatic inflammation, the overall response rate in the INTRON A plus ribavirin group is significantly greater with a two fold improvement over that observed with INTRON A plus placebo groups for all methods of evaluation.

Logistic regression analysis was done on all baseline demographic variables and disease characteristics. The only baseline statistically significant characteristic predictive of End of Follow-up sustained response was genotype other than 1.

TABLE 13

Sustained Virologic Response Rates by HCV Genotype for Study 2 Patients

| Genotype | Intron A + Ribavirin 24 weeks | 48 Weeks | Intron A + Placebo 48 Week |
|---|---|---|---|
| 1 | 18% (29/161) | 30% (48/159) | 11% (19/168) |
| 2 | 59% (16/27) | 74% (17/23) | 35% (8/23) |
| 3 | 66% (48/73) | 61% (45/74) | 32% (25/79) |
| 4–6 | 19% (3/16) | 38% (8/21) | 12% (1/8) |

The combination therapy provided higher sustained virologic response rate for all genotype compared to Intron A plus Placebo. Extending the duration of the combination therapy to 48 weeks increased the proportion of sustained virologic response for all genotypes except type 3. (See Table 13 as well as Table 15 for the combined vivologic response for studies 1 and 2)

For number of viral copies ($\leq 2$ million, >2 million), there was a numerical difference in favor of higher sustained virologic response rates in patients with $\leq 2$ million copies (Table 14). When genotype and baseline virus load are combined, a hierarchy of response is observed. Those patients with genotype other than 1 and baseline virus load $\leq 2$ million copies had the best End of Follow-Up response; those patients with genotype 1 and >2 million copies who received the longer 48 week treatment with combination therapy had the most significant improvement in substantial virologic response of all the groups.

Table 14 illustrates that extending the combination therapy to 48 weeks generally improved the sustained virologic response rates. The highest sustained virologic response rates were observed with patients who received the combination therapy for 48 weeks with genotypes other than 1 and initial HCV levels of $\leq 2$ million copies/mL. Importantly, for patients with genotype 1 and HCV levels >2 million, sustained virologic response rates with 48 weeks of combination therapy were more than 3 times higher than rates with only 24 week of the combination.

Conclusions on Efficacy for Combined Results for All Patients in Studies 1+2

Combination therapy was significantly more efficacious than INTRON®A monotherapy for initial treatment of chronic hepatitis C. Sustained virologic response rates in these antiviral treatment naive patients were almost three times higher with 48 weeks of combination therapy compared with 48 weeks of Intron A monotherapy and significantly higher with 48 weeks compared to 24 weeks of the combination therapy. The improvement in sustained response rates could be accounted for by two treatment effects: higher response rates at the end of treatment and decreased relapse rates. The net result of both of these effects was the highest sustained response rate with the 48 weeks of combination therapy compared to 48 weeks of monotherapy or a shorter regimen with the combination. This enhancement of efficacy with 48 weeks of combination therapy also included other measures of response such as biochemical (ALT) and histological endpoints.

In fact, sustained loss of serum HCV-RNA was highly correlated with other clinical endpoints—normalization of ALT and improvement in or resolution of hepatic inflammation. Loss of detectable HCV-RNA at the end of follow-up was associated with normalization of ALT in all treatment groups but was somewhat higher with combination therapy. The majority of combination therapy patients who were ALT normal were also HCV-RNA negative (83–87%).

Increased length of therapy had the greatest effect on relapse rates. At End of Follow Up, the relapse rates for both the 48 week combination and monotherapy treatment groups were lower than the relapse rate of the 24 week combination therapy treatment group. The combination of the high end of

TABLE 14

Disease Characteristics vs Sustained Virologic Response: All-Treated Patients in Study No. 2

| | Number (%) of Patients | | |
|---|---|---|---|
| Disease Characteristic | INTRON ® A 24 weeks | plus ribavirin 48 weeks | INTRON ® A plus Placebo 48 weeks |
| HCV-RNA/qPCR | | | |
| $\leq 2$ million copies/mL | 44% (48/108) | 47% (54/115) | 31% (15/49) |
| >2 million copies/mL | 28% (48/109) | 40% (64/102) | 13% (24/183) |
| HCV Genotype | | | |
| 1 | 18% (29/161) | 30% (48/159) | 11% (19/168) |
| Other Genotype | 58% (67/116) | 59% (70/118) | 31% (34/110) |
| Genotype/Baseline HCV-RNA/qPCR | | | |
| Other genotype/$\leq 2$ million copies/mL | 53% (28/53) | 62% (34/55) | 31% (15/49) |
| Other genotype/>2 million copies/mL | 62% (39/63) | 57% (36/63) | 31 % (19/61) |
| Genotype 1 & $\leq 2$ million copies/mL | 36% (20/55) | 33% (20/60) | 30% (14/46) |
| Genotype 1 & >2 million copies/mL | 8% (9/106) | 28% (28/99) | 4% (5/122) | treatment response resulting from 24 and 48 weeks of the combination therapy compared to 48 weeks of Intron A monotherapy and decreased relapse rates resulted in the highest sustained response rates. Sustained response rates were twice as high with 48 weeks of combination therapy compared with Intron A monotherapy(48) (p<0.001). Sustained virologic response rates were also higher with 48 weeks of combination therapy compared to only 24 weeks of the (p=0.008).

The benefit of combination therapy was maintained irrespective of standard predictors of response to INTRON®A monotherapy and 24-week combination therapy in relapsed patients. At entry to these trials, patients were stratified by the following disease characteristics: HCV genotype (type 1 or other genotypes); extent of HCV virus level (number of virus copies in the serum ≦2 million/mL or >2 million/mL); and cirrhosis (present or absent). Logistic regression analysis of sustained virologic response demonstrated that, in addition to treatment group, only HCV genotype was a significant predictor of sustained virologic response. Neither pretreatment HCV virus level nor presence of cirrhosis appeared to influence the ability of previously untreated patients to achieve sustained virologic response to the combination therapy.

With 48 weeks of combination therapy, sustained response rates were consistently higher than those for 48 weeks of Intron A monotherapy regardless of genotype and were generally higher than 24 weeks of combination therapy. As a group, patients infected with genotype 1 have been shown to be less responsive to INTRON®A monotherapy than patients infected wit other genotypes. Despite this, sustained virologic response rates for genotype 1 were approximately 3 times higher with 48 weeks of combination therapy compared to 48 weeks of Intron A monotherapy and almost twice as high with 48 weeks compared to 24 weeks of combination therapy. The combination therapy consistently produced higher sustained virologic response rates in patients infected with other genotypes. Response rates with both 24 and 48 weeks of combination therapy were higher than with 48 weeks of Intron A monotherapy and in all genotypes except types 2 & 3 which genotypes had the same response rate i.e., about 64% at the end of 24 weeks as well as after 48 weeks of combination therapy), extending the duration of the combination therapy to 48 weeks increased the proportion of patients with sustained virologic responses. (See Table 15)

The combination therapy was also more effective than 48 weeks of Intron A monotherapy in producing sustained virologic responses regardless of virus level at Baseline. Forty-eight weeks of combination therapy consistently produced higher sustained virologic response rates at every level of virus infection than 48 weeks of Intron A monotherapy. Sustained response rates were similar for most virus levels in both the 24 and 48 week combination therapy treatment groups, except with the highest virus levels (5–<6 and ≧6×10$^6$ copies/mL) where sustained response rates with the 48 week combination therapy groups were approximately twice as high as the 24 week combination therapy groups.

As noted previously, patients with genotypes other than type 1 had higher sustained virologic response rates than those with type 1 and a virus level ≦2 million/mL was associated with a better response rate than >2 million/mL. It was notable that extending the combination therapy treatment to 48 weeks improved the sustained response rates for patients expected to have the lowest response rates, namely, those with genotype 1 and >2 million copies of HCV-RNA/ mL. Extending the combination therapy to 48 weeks in this group of patients produced sustained virologic response rates that were 4 times higher than those with only 24 weeks of combination therapy.

Other demographic/disease history characteristics had little effect on outcome with combination therapy. In contrast, considerably lower sustained response rates were noted with 48 weeks of Intron A monotherapy in patients older than 55 years, >75 kg or who were infected through transfusion. All had sustained response rates in the range of 10–12%.

Availability of paired biopsies was high compared with similar types of studies in chronic hepatitis C patients. As anticipated, pre- and/or posttreatment liver biopsies were unavailable for a proportion of patients for a variety of reasons. However, paired biopsies were obtained from 71% of patients. Improvement was noted in a significantly higher proportion of 48 week combination therapy patients compared with the 48 week Intron A monotherapy patients at End of Follow Up (p<0.001). Twenty-four weeks of combinatin therapy also was significantly more efficacious than 48 weeks of Intron A monotherapy in improving hepatic inflammation. As noted previously, the correlation with virologic response was maintained whether biopsies were assessed by improvement or mean change from baseline in necroinflammatory score; 64–69% of patients had improvement in hepatic inflammation with mean changes from baseline of –3.8 to –5.0. The most substantial mean change was in the 48 week Intron A monotherapy patients.

As anticipated, sustained virologic responders in all treatment groups experienced greater improvement in liver biopsy inflammation scores than patients who remained HCV-RNA positive, and although the extent of improvement was similar in all groups the proportion of virologic responders with histologic improvement was at least twice as high with both the 24 and 48 weeks of combination therapy than with 48 weeks of Intron A monotherapy. Extending the combination therapy resulted in higher mean improvements in hepatic inflammation. It is also interesting to note that patients who relapsed from the 48 week combination therapy had considerable mean improvement in inflammation. The combined results are summarized in Tables 15 to 20.

TABLE 15

Combined Virologic Response for Studies 1 and 2
Efficacy: Loss of Delectable HCV-RNA at End of Treatment
(EOT and Sustained Virologic Response At End of Follow Up
(EOFU) and Percent Patients Responding

|  | Intron A + Ribavirin | | Intron A + Placebo | | | |
| --- | --- | --- | --- | --- | --- | --- |
|  | 24 weeks | 48 weeks | 24 weeks | 48 weeks | P Value | |
| No. of Patients[1] | N = 505 A | N = 505 B | N = 231 C | N = 503 D | B vs D | A vs D |
| EOT[2] | 53% | 50% | 29% | 24% | <0.001 | <0.001 |
| EOFU[3] | 33% ± 4 | 41% ± 5 | 6% | 16% | <0.001 | <0.001 |
| HCV Genotype | (No. of Patients) | (No. of Patients) |  |  |  |  |
| Type 1 | 17% ± 4 (56/326) | 29% ± 5 (94/325) | 2% | 9% |  |  |
| 2 | 73% ± 12[4] (41/57) | 70% ± 12[4] (42/60) | 18% | 35% |  |  |
| 3 | 63% ± 9[4] (64/101) | 62% ± 10[4] (60/97) | 8% | 29% |  |  |

TABLE 15-continued

Combined Virologic Response for Studies 1 and 2
Efficacy: Loss of Delectable HCV-RNA at End of Treatment
(EOT and Sustained Virologic Response At End of Follow Up
(EOFU) and Percent Patients Responding

|  | Intron A + Ribavirin | | Intron A + Placebo | | |
|---|---|---|---|---|---|
|  | 24 weeks | 48 weeks | 24 weeks | 48 weeks | P Value |
| Types 4/5/6 | 24% ± 10 (5/21) | 39% ± 20 (9/23) | 0% | 11% | |

[1]Patient characteristics: (a) 66% male; 34% female; (b) mean age: 42.7 yrs; (c) Mean pretreatment HCV-RNA levels < 2 million copies/ml: 34%, and > 2 million copies/ml: 66%; Super Quant, NGI; (d) HCV genotype 1 = 66%; genotype 2 = 13%, non 1–3=3%.
[2]EOT is End of Treatment.
EOFU is End of Follow-Up - 24 weeks posttreatment; P value A vs B = 0.257;
[3]Sustained virologic response at End of Follow-Up; P Value A vs B = 0.008
[4]The sustained virologic response for HCV genotypes 2 and 3 at the end of 24 weeks was about 64.5% and at the end of 48 weeks was about 65%.

TABLE 16

Percentage of Sustained Virologic Response for All HCV-Genotype 1 Patients

|  | Intron A + Ribavirin | | Intron A + Placebo | |
|---|---|---|---|---|
| Patient | 24 weeks | 48 weeks | 24 weeks | 48 weeks |
| HCV-Genotype 1 and ≤ 2 million copies/mL | 32% | 33% | 4% | 25% |
| HCV Genotype 1 and > 2 million copies/mL | 10% | 27% | 1% | 33% |
| All HCV-Genotypes 1 | 17% | 29% | 2% | 9% |

The sustained virologic response for all HCV genotype 1 patients treated for 24 and 48 weeks with the Combination Therapy was statistically significantly superior to that observed for all HCV genotype 1 patients treated with INTRON A plus placebo for 24 and 48 weeks. The sustained virologic response for HCV-genotype 1 patients with a baseline HCV viral load of greater than 2 million copies/mL was statistically significantly superior at 24 and 48 weeks of Combination Therapy compared to INTRON A+Placebo for 24 and 48 weeks.

TABLE 17

Sustained Virologic Response by HCV - Genotype and Baseline HCV-RNA Levels for Studies 1 & 2

|  | Intron A + Ribavirin | | Intron A + Placebo | |
|---|---|---|---|---|
| Patients | 24 weeks | 48 weeks | 24 weeks | 48 weeks |
| HCV Genotype 1 and Baseline HCV-RNA levels of ≤ 2 million copies/mL | 32% | 33% | 4% | 25% |
| HCV Genotype 1 and Baseline HCV-RNA levels of > 2 million copies/mL | 11% | 27% | 1% | 4% |
| Other HCV Genotypes[1] and Baseline HCV-RNA levels of > 2 million | 61% | 64% | 25% | 36% |
| Other HCV Genotypes[1] and Baseline HCV-RNA levels of > 2 million copies | 62% | 61% | 11% | 10% |

[1]HCV-genotypes 4/5/6 account for 3% of patients Sustained Response for I + R: 24% (24 wks) and 38% (48 weeks) for I + P: 0% (24 weeks) and 11% (48 weeks) Sustained Response Rate for HCV-Genotypes 2 + 3 is same as above

TABLE 18

Sustained Virologic Response by Baseline HCV-RNA Levels for ALL Patients (Studies 1 & 2)

|  | Intron A + Ribavirin | | Intron A + Placebo | |
|---|---|---|---|---|
| Patients | 24 weeks | 48 weeks | 24 weeks | 48 weeks |
| Patients with Baseline HCV-RNA Levels ≤ 2 million copies/mL | 44% | 46% | 9% | 36% |
| Patients with Baseline HCV-RNA Levels > 2 million copies/mL | 27% | 38% | 4% | 10% |

TABLE 19

Percent of Sustained Virologic Responders by Time to First No Detectable HCV-RNA Levels for Studies 1 & 2

| Time to First No-Detectable HCV-RNA (Weeks) | Intron A + Ribavirin | | Intron A + Placebo | |
|---|---|---|---|---|
|  | 24 weeks | 48 weeks | 24 weeks | 48 weeks |
| 4 | 83% (92/111) | 82% (94/115) | 48% (10/21) | 71% (47/66) |
| 12 | 44% (66/149) | 66% (91/137) | 9% (3/32) | 35% (29/84) |
| 24 | 19% (8/42) | 44% (20/45) | 0% (0/22) | 15% (6/39) |

TABLE 20

ALT Response: Normalization of Serum ALT in All Patients from Studies 1 & 2

| | INTRON A + Ribavirin | | INTRON A + Placebo | | | |
| --- | --- | --- | --- | --- | --- | --- |
| Study | A 24 weeks (N = 505) | B 48 weeks (N = 505) | C 24 weeks (N = 231) | D 48 weeks (N = 503) | P[a] Value B vs D | P[a] Value A vs D |
| At End of Treatment | | | | | | |
| 1 & 2[b] | 66% (329) | 66% (334) | 24% (56) | 37% (185) | <0.001 | 0.739 |
| 1 | 58% (133) | 61% (138) | 24% (56) | 28% (82) | <0.001 | <0.001 |
| 2 | 71% (196) | 71% (196) | — | 44% (123) | <0.001 | <0.001 |
| End of Follow-Up | | | | | | |
| 1 + 2[b] | 36% (181) | 44% (221) | 11% (25) | 24% (102) | <0.001 | <0.001 |
| 1 | 32% (72) | 36% (83) | 11% (25) | 16% (35) | <0.001 | <0.001 |
| 2 | 39% (109) | 50% (138) | — | 24% (67) | <0.001 | <0.001 |

[a]Cochran-Mantet Haenszel general association for combined results; Fisher's Exact Test for individual studies.
[b]Combined results Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of treating antiviral treatment naive patients having chronic hepatitis C ("HCV") infection comprising identifying antiviral treatment naive patients having HCV genotype 1 and an initial viral load of greater than 2 million copies/ mL of serum HCV-RNA as measured by HCV-RNA/ quantitative Polymerase Chain Reaction ("qPCR") and then administering to said antiviral treatment naive patients a therapeutically effective amount of ribavirin and a therapeutically effective amount of interferon-alpha for a time period of about 40 to about 50 weeks and identifying antiviral treatment naive patients having an HCV genotype 1 and an initial viral load of less than or equal to 2 million copies/ mL of serum HCV-RNA as measured by HCV-RNA/ quantitative Polymerase Chain Reaction ("qPCR") and then administering to said antiviral treatment naive patients a therapeutically effective amount of ribavirin and a therapeutically effective amount of interferon-alpha for a time period of about 20 to about 24 weeks.

2. The method of claim 1, wherein the antiviral treatment naive patients known to be HCV-genotype 1 are treated for about 48 weeks, and the effective amount of ribavirin administered is from about 800 to about 1200 mg per day.

3. The method of claim 1, wherein the interferon-alpha is selected from interferon alpha-2a, interferon alpha 2b, a consensus interferon, a purified interferon alpha product, a pegylated interferon alpha-2a, or a pegylated interferon alpha 2b.

4. The method of claim 1, wherein the interferon-alpha is selected from interferon alpha-2a, interferon alpha 2b, a consensus interferon, or a purified interferon alpha product, and the amount of interferon-alpha administered is from about 2 to about 10 million International United ("IU") per week on a weekly, three times a week ("TIW"), five times a week ("QOD") or daily basis.

5. The method of claim 1, wherein the interferon-alpha is interferon alpha 2b, and the amount of interferon-alpha administered is from about 3 million IU TIW.

6. The method of claim 1, wherein the interferon-alpha administered is consensus interferon and the amount of interferon-alpha administered is from about 1 to about 20 micrograms per week on a weekly, TIW, QOD or daily basis.

7. The method of claim 1, wherein the interferon-alpha administered is a pegylated interferon alpha-2b and the amount of interferon-alpha administered is from about 0.5 to about 2.0 micrograms/kilogram per week on a weekly, TIW, QOD or daily basis.

8. The method of claim 1, wherein the interferon-alpha administered is a pegylated interferon alpha-2a and the amount of interferon-alpha administered is from about 20 to about 250 micrograms/kilogram per week on a weekly, TIW, QOD or daily basis.

9. A method of treating antiviral treatment naive patients having chronic hepatitis C ("HCV") infection comprising identifying antiviral treatment naive patients having an HCV genotype 1 and an initial viral load of greater than 2 million copies/ ML of serum HCV-RNA as measured by HCV-RNA/ quantitative Polymerase Chain Reaction ("qPCR") and then administering to said antiviral treatment naive patients a therapeutically effective amount of ribavirin and a therapeutically effective amount of interferon-alpha for a time period of about 48 weeks and identifying antiviral treatment naive patients having an HCV genotype 1 and an initial viral load of less than or equal to 2 million copies/mL of serum HCV-RNA as measured by HCV-RNA/ quantitative Polymerase Chain Reaction ("qPCR") and then administering to said antiviral treatment naive patients therapeutically effective amount of ribavirin and a therapeutically effective amount of interferon-alpha for a time period of at least about 24 weeks and up to about 48 weeks.

10. A method of treating antiviral treatment naive patients having chronic hepatitis C ("HCV") infection comprising identifying antiviral treatment naive patients having an HCV genotype 2 or 3 and administering to said antiviral treatment naive patients a therapeutically effective amount of ribavirin and a therapeutically effective amount of interferon-alpha for a time period of at least about 20 weeks to about 24 weeks.

11. A method of treating antiviral treatment naive patients having chronic hepatitis C ("HCV") infection comprising identifying antiviral treatment naive patients having an HCV genotype 2 or 3 and administering to said antiviral treatment naive patients a therapeutically effective amount of ribavirin and a therapeutically effective amount of interferon-alpha for a time period of at least about 24 weeks.

12. The method of claim 10 or 11, wherein the antiviral treatment naive patients known to be HCV-genotype 2 or 3 are treated for about 24 weeks, and the effective amount of ribavirin administered is from about 800 to about 1200 mg per day.

13. The method of claims 9 or 10 or 11, wherein the interferon-alpha is selected from interferon alpha-2a, interferon alpha 2b, a consensus interferon, a purified interferon alpha product, a pegylated interferon alpha-2a, or a pegylated interferon alpha 2b.

14. The method of claims 9 or 10 or 11, wherein the interferon-alpha is selected from interferon alpha-2a, interferon alpha 2b, a consensus interferon, or a purified interferon alpha product, and the amount of interferon-alpha administered is from 2 to 10 million IU per week on a weekly, TIW, QOD, or daily basis.

15. The method of claims 9 or 10 or 11, wherein the interferon-alpha is interferon alpha 2b, and the amount of interferon-alpha administered is from 3 million IU, TIW.

16. The method of claims 9 or 10 or 11, the interferon-alpha administered is consensus interferon and the amount of interferon-alpha administered is from 1 to 20 micrograms per week on a weekly, TIW, QOD or daily basis.

17. The method of claims 9 or 10 or 11, wherein the interferon-alpha administered is a pegylated interferon alpha-2b and the amount of interferon-alpha administered is from 0.5 to about 2.0 micrograms/kilogram per week on a weekly, TIW, QOD or daily basis.

18. The method of claims 9 or 10 or 11, wherein the interferon-alpha administered is a pegylated interferon alpha-2a and the amount of interferon-alpha administered is from 20 to about 250 micrograms/kilogram per week on a weekly, TIW, QOD or daily basis.

19. The method of claims 9 or 10 or 11, wherein the effective amount of ribavirin administered is from about 800 to about 1200 mg per day.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (oligonucleotide)

(xi) SEQUENCE DESCRIPTION: SEQ ID NO:1:

GTGGTCTGCG GAACCGGTGA GT      22

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (oligonucleotide)

(xi) SEQUENCE DESCRIPTION: SEQ ID NO:2:

TGCACGGTCT ACGAGACCTC      20

(2) INFORMATION FOR SEQ ID NO:3:

(i) SEQUENCE CHARACTERISTICS:
      (A) LENGTH: 21 base pairs
      (B) TYPE: nucleic acid
      (C) STRANDEDNESS: single -continued

```
        (D) TOPOLOGY: linear (ii) MOLECULE TYPE: DNA (oligonucleotide)

(xi) SEQUENCE DESCRIPTION: SEQ ID NO:3:

CTGTGAGGAA CTACTGTCTT C                                                    21

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:4:

CCCTATCAGG CAGTACCACA A                                                    21
```